United States Patent [19]

Griffith

[11] 4,300,940
[45] Nov. 17, 1981

[54] METHOD AND COMPOSITION FOR TREATING SOIL TO SUPPRESS THE NITRIFICATION OF AMMONIUM NITROGEN THEREIN

[75] Inventor: Jeffrey D. Griffith, Lafayette, Calif.

[73] Assignee: The Dow Chemical Company, Midland, Mich.

[21] Appl. No.: 59,085

[22] Filed: Jul. 19, 1979

[51] Int. Cl.$^3$ ............................................. C05G 3/08
[52] U.S. Cl. .......................................... 71/27; 71/28; 71/59
[58] Field of Search ...................... 71/11, 28, 59, 122, 71/1, 7, 27; 560/254; 568/812; 260/456 R, 456 A

[56] References Cited

U.S. PATENT DOCUMENTS 3,900,509  8/1975  Markley .............................. 560/254
3,972,913  8/1976  Markley .............................. 568/812

*Primary Examiner*—William F. Smith
*Attorney, Agent, or Firm*—Merlin B. Davey

[57] ABSTRACT

Soil nitrogen is conserved and plant nutrition improved by treating plant growth media with certain phenyl substituted butane diols, or phenylbutyl carboxylic or sulfonic acids such as ethanesulfonic acid-4,4,4-trichloro-2-hydroxy-2-phenylbutyl ester.

5 Claims, No Drawings

METHOD AND COMPOSITION FOR TREATING SOIL TO SUPPRESS THE NITRIFICATION OF AMMONIUM NITROGEN THEREIN

BACKGROUND OF THE INVENTION

The nature of the agricultural problem for which the present invention constitutes a remedy has previously been discussed in the prior art. See, for example, U.S. Pat. Nos. 3,050,380; 3,135,594 and 3,533,774.

The present standard nitrification inhibitor on the market is 2-chloro-6-trichloromethyl pyridine (nitrapyrin). Because of loss by volatilization from treated fertilizers during storage, the use of this compound has tended to be restricted to applications where it can be applied simultaneously with fertilizer, for example, with anhydrous and aqueous ammonia. However, in many parts of the world, fertilizers are applied largely in the solid form, and, in such applications, it is desired to employ a nitrification inhibitor having less volatility and greater persistence.

DESCRIPTION OF THE PRIOR ART

It has been common practice for improving plant nutrition and conserving soil nitrogen to treat plant growth media with a (trichloromethyl)pyridine compound, i.e., a compound having a pyridine nucleus and being substituted thereon by at least one trichloromethyl group as taught in U.S. Pat. No. 3,135,594. Among the suitable compounds are those containing chlorine or methyl substituents on the pyridine nucleus in addition to a trichloromethyl group and are inclusive of chlorination products of methylpyridines such as lutidine, collidine and picoline.

The compounds found to be useful in the method of the present invention have been disclosed in U.S. Pat. No. 3,900,509 and may be prepared by the methods taught therein.

SUMMARY OF THE INVENTION

It has now been found that soil nitrogen may be conserved and plant nutrition improved by treating plant growth media with phenylbutyl compounds having the formula

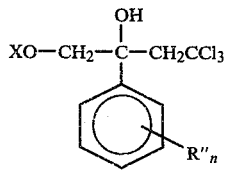

wherein X is hydrogen, $RSO_2$— or $R'CO$—; wherein R is alkyl of 1 to 16 carbon atoms, chloroalkyl, phenyl, halophenyl, nitrophenyl, amino or alkylamino wherein the alkyl group contains 1 to 8 carbon atoms; $R'$ is alkyl of 1 to 4 carbon atoms or phenyl and $R''$ is 3, 4 or 5 ring substituted chloro or alkyl of 1 to 4 carbon atoms and n is 0, 1 or 2.

DETAILED DESCRIPTION OF THE INVENTION

By the practice of this invention, the nitrification of ammonium nitrogen in the soil to nitrate nitrogen is suppressed thereby preventing the rapid loss of ammonium nitrogen from the soil. Furthermore, by proper distribution of the above compounds, hereinafter called "active ingredients", this action of inhibiting the transformation of ammonium nitrogen to nitrate nitrogen is effective over a prolonged period of time including those situations where treated fertilizer is stored for some time before use. The ammonium nitrogen may arise from added ammonium nitrogen fertilizers or be formed in the soil by conversion of the organic nitrogen constituents found in soil or added thereto as components of organic fertilizers.

The provision of an effective but sublethal dosage of the active ingredients in the soil or growth medium is essential for the practice of the present invention. In general, good results are obtained when the growth medium is impregnated with the active ingredient in the amount of from about 0.05 part to about 4000 parts or more by weight per million parts by weight of growth medium. (hereinafter, the abbreviation ppm when employed is meant to designate parts by weight of active ingredient per million parts by weight of soil or growth medium.) The preferred amounts to be employed are dependent upon the particular situation. Thus, in determining the amount to be employed, consideration is made not only of the treatment need, i.e., soil pH and temperature, soil type, etc. but also of the mode of application to soil. When the active ingredient is to be applied in a broadcast application, the concentration may frequently be less than in row or band application where for a substantial depth and width within the vicinity of application there may be a very high concentration of the active ingredient. When application is made near the root zone of growing plants or when application is made immediately prior to seeding or transplanting, the amounts supplied are frequently at a lower rate than when application is made at the end of the growing season to prepare the soil for the following season. By dispersing very large dosages in growth media, a prolonged inhibition of nitrification may be obtained over a period of many months. The concentration of the active ingredient is eventually reduced to a minimum by decomposition in the soil.

In one method for carrying out the present invention, the active ingredient is distributed throughout the growth media in a broadcast application such as by spraying, dusting, distributing in irrigation water, etc. In such application, the active ingredient is supplied in amounts sufficient to permeate the growing area of soil with an amount of from about 0.05 to about 1000 p.p.m. In field administration, the active ingredient may be distributed in the soil in the amount of at least 0.05 pound per acre and through such cross-section of the soil as to provide for the presence therein of an effective concentration of the agent. It is usually preferred that the active ingredient be distributed to a depth of at least three inches below the soil surface and at a dosage of at least 0.05 pound per acre 3-inch of soil.

In another method for carrying out the present invention, the active ingredient is administered to the growth medium in a band or row application. In such application, administration is made with or without carrier in amount sufficient to supply to soil or growth medium a concentration which may be as high as 4000 ppm or more. After administration with or without discing or dragging, subsequent irrigation or rainfall distributes the active ingredient throughout the growth medium.

In one embodiment of the present invention, the active ingredient is distributed throughout the growth media prior to seeding or transplanting the desired crop plant.

In another embodiment, the soil in the root zone of growing plants is treated with the active ingredient in an amount effective to inhibit nitrification. Oftentimes it is desirable to treat the soil adjacent to plants, and this procedure may be carried out conveniently in side-dressing operations.

In a further embodiment, soil may be treated with the compounds following harvest or after following to prevent rapid loss of ammonium nitrogen and to build up the ammonium nitrogen formed by conversion of organic nitrogen compounds. Such practice conserves the soil nitrogen for the following growing season. In such application, the upper treatment limit is primarily an economic consideration.

In an additional embodiment, the soil is treated with the active ingredient in conjunction with the application of reduced nitrogen fertilizers. The treatment with the active ingredient may be carried out prior to, subsequent to or simultaneously with the application of fertilizers. Such practice prevents the rapid loss of the ammonium nitrogen added as fertilizer and of the ammonium nitrogen formed from organic nitrogen in fertilizers by the action of soil bacteria. The administration to the soil of the active ingredient in an ammonium nitrogen fertilizer composition constitutes a preferred embodiment of the present invention.

The present invention may be carried out by distributing the active ingredient or compound in an unmodified form through growth medium. The present method also embraces distributing the compound as a constituent in liquid or finely divided solid compositions. In such practice, the compound may be modified with one or more additaments or soil treating adjuvants including water, petroleum distillates or other liquid carriers, surface-active dispersing agents, finely divided inert solids and nitrogen fertilizers. Depending upon the concentration of the compound, such augmented composition may be distributed in the soil without further modification or be considered a concentrate and subsequently diluted with additional inert carrier to produce the ultimate treating composition. The required amount of the compound may be supplied to growth media in from 1/24 to 50 gallons of organic solvent carrier, in from 5 to 27,000 or more gallons of aqueous carrier or in from about 20 to 2,000 pounds of solid carrier per acre treated. When an organic solvent carrier is employed, it may be further dispersed in the above volume of aqueous liquid carrier.

The concentration of the compound in compositions to be employed for the treatment of growth media is not critical and may vary considerably provided the required dosage of effective agent is supplied to the growth media. The concentration of the compound may vary from 0.00001 percent by weight to 95 percent by weight of the composition, depending on whether the composition is a treating composition or a concentrate composition and whether it is in the form of a solid or a liquid. In aqueous liquid treating compositions, concentrations of from 0.00001 percent to 0.25 percent by weight of the compound are considered the preferred composition. The concentration of the compound in organic solvents may be from about 2 to 95 percent by weight. Concentrate liquid compositions generally contain from about 2.5 to 95 percent by weight of the compound. Treating compositions generally contain 0.0001 percent to 10 percent by weight of the compound.

Liquid compositions containing the desired amount of the compound may be prepared by dispersing the latter in one or more liquid carriers such as water or an organic solvent, with or without the aid of a suitable surface-active dispersing agent or emulsifying agent. Suitable organic solvents include acetone, diisobutylketone, methanol, ethanol, isopropyl alcohol, diethyl ether, toluene, methylene chloride, chlorobenzene and the petroleum distillates. The preferred organic solvents are those which are of such volatility that they leave little permanent residue in the soil. When the solutions of the compound in organic solvents are to be further diluted to produce aqueous dispersions, the preferred solvents include acetone and the alcohols. When the liquid carrier is entirely organic in nature, particularly desirable carriers are the petroleum distillates boiling almost entirely under 400° F. at atmospheric pressure and having a flash point above about 100° F. Dispersing and emulsifying agents which may be employed in liquid compositions include condensation products of alkylene oxides with phenols and organic acids, alkyl aryl sulfonates, polyoxyalkylene derivatives of sorbitan esters, complex ether alcohols, mahogany soaps and the like. The surface-active agents are generally employed in the amount of from about 1 to 20 percent by weight of the compound.

Solid compositions containing the active compound may be prepared by dispersing the latter in finely divided inert solid carriers such as talc, chalk, gypsum, vermiculite, bentonite and the like, fuller's earth, attapulgite and other clays, various solid detergent dispersing agents and solid fertilizer compositions. In preparing such compositions, the carrier is mechanically ground with the compound or wet with a solution or dispersion thereof in a volatile organic solvent. Depending upon the proportions of ingredients, these compositions may be employed without further modification or be considered concentrates and subsequently further diluted with a solid surface-active dispersing agent, talc, chalk, gypsum, or the like to obtain the desired treating composition. Furthermore, such concentrate compositions may be dispersed in water with or without added dispersing agent or agents to prepare aqueous soil treating compositions.

Soil treatment compositions may be prepared by dispersing the compound in fertilizers such as ammonium fertilizer or organic nitrogen fertilizer. The resulting fertilizer composition may be employed as such or may be modified as by dilution with additional nitrogen fertilizer or with inert solid carrier to obtain a composition containing the desired amount of active agent for treatment of soil. Further, an aqueous dispersion of the compound-fertilizer composition may be prepared and administered to the growth medium. Fertilizer compositions comprising the compound in intimate admixture with ammonium fertilizers constitute preferred embodiments of the present invention.

In fertilizer compositions comprising a reduced nitrogen fertilizer, it is desirable that the compound be present in an amount of at least about 0.05 percent by weight based on the weight of the nitrogen present in the fertilizer as reduced nitrogen and may be present in amounts as high as 95 percent by weight of the reduced nitrogen in the fertilizer. Thus, when a fertilizer composition contains both reduced nitrogen and other forms of nitrogen such as in the case of ammonium nitrate fertilizer compositions, the amount of compound is based on the weight of nitrogen present in the ammonium component.

In operations carried out in accordance with the present invention, the soil may be treated in any convenient fashion with the active compound or a composition containing the latter. For example, these modified or unmodified compositions may be mechanically mixed with the soil; applied to the surface of soil and thereafter dragged or disced into the soil to a desired depth; or transported into the soil with a liquid carrier such as by injection, spraying or irrigation. When the distribution is carried out by introducing the compound in the water employed to irrigate the soil, the amount of water is varied in accordance with the moisture content of the soil in order to obtain a distribution of the compound to the desired depth. The compound may be readily and conveniently distributed to a depth of a few inches to four feet by irrigation methods. The preferred method embrace procedures using any of these steps or combination of steps wherein the compound is distributed in the soil substantially simultaneously with a reduced nitrogen fertilizer.

The following examples further illustrate the invention but are not to be construed as limiting.

A number of compounds were tested for their ability to reduce the rate of nitrification of ammonium nitrogen applied as urea to soil and their activity, relative to the standard 2-chloro-6-trichloromethylpyridine, is reported in the following table.

The test method comprised selecting a soil which had a low nitrate concentration and good nitrification activity. A sufficient volume of water was added to 50 g of the soil in a wide-mouth, screw-cap, 240-ml, glass bottle, such that the moisture content of the mixture was made equal to the ⅓ bar tension value for that soil. The mixture was thoroughly stirred with a spatula before sealing. The added water contained 10 mg (200 ppm) of nitrogen in the form of urea (21.4 mg of urea) and 100 μg (2 ppm based on dry soil weight) of test chemical. When the test chemical had a low water solubility, it was compounded in acetone (or other suitable solvent) in such a way that the final mixture in the soil contained no more than 10 μl of acetone. Acetone slows the rate of soil nitrification and its concentration must be carefully controlled. Single samples of each test chemical were incubated for 2 weeks at 21° C.

The experiment comprised the following types of samples:

1. Nitrate blank containing soil, water and solvent only.
2. Nitrogen standard containing soil, water, urea and solvent, in duplicate and values averaged.
3. Chemical standard containing soil, water, urea, solvent, and nitrapyrin as the standard for comparison, in duplicate, and values averaged.
4. Test chemicals containing soil, water, urea, solvent, and test chemical. Single samples.

The soil samples were analyzed as follows: Sufficient saturated calcium sulfate solution was added to the sample, such that the total volume of added water was 100 ml (included water added during sample preparation). The capped mixture was shaken 10 minutes to solubilize nitrate, the soil particulates were allowed to settle, and the calcium sulfate solution was decanted. The nitrate concentration in the water phase was determined with a nitrate-specific ion electrode such as Orion Model 93-07.

The non-nitrate nitrogen remaining in the soil after 2 weeks (performance value) was calculated as follows:

Percent non-nitrate $N$ remaining in soil =

$$200 \text{ ppm} - \frac{\text{(Sample nitrate } N \text{ ppm} - \text{ soil blank nitrate } N \text{ ppm)} \times 100 \text{ ml}}{\frac{50 \text{ g}}{200 \text{ ppm}}} \times 100.$$

= 100 − (Sample nitrate $N$ ppm − soil blank nitrate $N$ ppm).

The performance value for each sample in the experiment was converted to a net performance value by subtracting the average performance value of the solvent-soil check replicates (No. 2 above).

An activity ratio (or percent) was calculated for each test chemical as follows:

$$\frac{\text{Net performance value of test chemical}}{\text{Net performance value of nitrapyrin}} = \text{Activity ratio.}$$

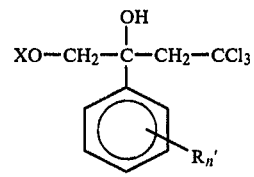

TABLE I

| Compound | X | R' | Activity % at 2 ppm |
|---|---|---|---|
| 1 | $C_2H_5SO_2$ | — | 100 |
| 2 | $i\text{-}C_3H_7SO_2$ | — | 100 |
| 3 | $Cl(CH_2)_3SO_2$ | — | 100 |
| 4 | $NH_2SO_2$ | — | 100 |
| 5 | $CH_3SO_2$ | — | 90 (5 ppm) |
| 6 | $C_{16}H_{33}SO_2$ | — | 100 (100 ppm) |
| 7 | $C_4H_9SO_2$ | — | 90 |
| 8 | $CH_3SO_2$ | 3,5-di$CH_3$ | 50 |
| 9 | $CH_3SO_2$ | 3-Cl | 75 (5 ppm) |
| 10 | $i\text{-}C_3H_7NHSO_2$ | — | 100 |
| 11 | $CH_3CO$ | — | 100 |
| 12 | $C_6H_5CO$ | 4-$CH_3$ | 100 |
| 13 | H | — | 100 |
| 14 | H | 3,5-diCl | 100 |
| 15 | $4\text{-}Br\text{-}C_6H_4SO_2$ | — | 100 |
| 16 | $4\text{-}NO_2\text{-}C_6H_4SO_2$ | — | 100 |

What is claimed is:

1. A method for suppressing the nitrification of ammonium nitrogen in growth media which comprises treating said growth media with a compound having the formula

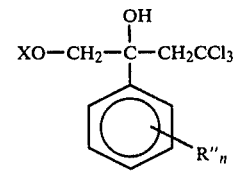

wherein X is hydrogen, or R'CO—; wherein R' is alkyl of 1 to 4 carbon atoms or phenyl and R" is 3, 4 or 5 ring substituted chloro or alkyl of 1 to 4 carbon atoms and n is 0, 1 or 2.

2. Method of claim 1 wherein the compound is dispersed in the growth media in an effective amount of from 0.05 to 4000 parts by weight per million parts by weight of growth media.

3. A fertilizer composition useful for suppressing the nitrification of ammonium nitrogen in growth media and for preventing rapid loss of ammonium nitrogen therefrom comprising a reduced nitrogen fertilizer and a compound having the formula

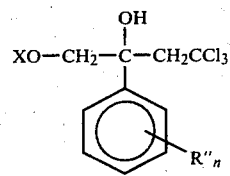

wherein X is hydrogen, or R'CO—; wherein R' is alkyl of 1 to 4 carbon atoms or phenyl and R" is 3, 4 or 5 ring substituted chloro or alkyl of 1 to 4 carbon atoms and n is 0, 1 or 2.

4. Composition of claim 3 wherein X is H, R" is chloro and n is 2.

5. Composition of claim 4 wherein the chlorines are substituted in the 3 and 5 positions of the phenyl radical.

* * * * *